United States Patent
Jarrousse et al.

(10) Patent No.: US 10,649,236 B2
(45) Date of Patent: May 12, 2020

(54) OPHTHALMIC LENS AND METHOD FOR DETERMINING SUCH AN OPHTHALMIC LENS

(71) Applicant: ESSILOR INTERNATIONAL (COMPAGNIE GENERALE D'OPTIQUE), Charenton-le-Pont (FR)

(72) Inventors: Marie Jarrousse, Charenton-le-Pont (FR); Céline Benoit, Charenton-le-Pont (FR); Damien Paille, Charenton-le-Pont (FR); Bruno Decreton, Charenton-le-Pont (FR); Eva Lazuka-Nicoulaud, Charenton-le-Pont (FR); Claire-Eline Bres, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 121 days.

(21) Appl. No.: 15/565,477

(22) PCT Filed: Apr. 8, 2016

(86) PCT No.: PCT/EP2016/057841
§ 371 (c)(1),
(2) Date: Oct. 10, 2017

(87) PCT Pub. No.: WO2016/162533
PCT Pub. Date: Oct. 13, 2016

(65) Prior Publication Data
US 2018/0081199 A1    Mar. 22, 2018

(30) Foreign Application Priority Data
Apr. 10, 2015   (EP) .................................... 15305542

(51) Int. Cl.
*G02C 7/10* (2006.01)
*G02C 7/02* (2006.01)
*G02C 7/06* (2006.01)

(52) U.S. Cl.
CPC ............... *G02C 7/104* (2013.01); *G02C 7/02* (2013.01); *G02C 7/025* (2013.01); *G02C 7/027* (2013.01); *G02C 7/066* (2013.01)

(58) Field of Classification Search
None
See application file for complete search history.

(56) References Cited

U.S. PATENT DOCUMENTS

2003/0231281 A1 * 12/2003 Fuschi ..................... G02C 7/06
351/159.48
2004/0027679 A1    2/2004 Welk et al.
(Continued)

FOREIGN PATENT DOCUMENTS

EP    2369403    9/2011
EP    2829905    1/2015
(Continued)

OTHER PUBLICATIONS

Anderson et al. "Minus lens simulated accommodative amplitude decreases sigmoidally with age: a study of objectively measured accommodative amplitude from age 3," *Investigative Ophthalmology & Visual Science*, 49(7):2919-2926, (2008).
(Continued)

*Primary Examiner* — William R Alexander
*Assistant Examiner* — Gary W O' Neill
(74) *Attorney, Agent, or Firm* — Norton Rose Fulbright US LLP

(57) ABSTRACT

The invention relates to a method of selection of an ophthalmic lens suitable for correcting at least an optical impairment of an eye of a wearer who observes a screen. According to the invention the method comprises the steps of:
(Continued)

determining at least a characteristic of posture of the wearer observing said screen, determining a dioptric power value associated to said vision zone allowing the wearer when wearing the ophthalmic lens to have an easier reading of said screen, determining at least one characteristic of filtering means to adjust the light exposure of the wearer to said screen, and determining the vision zone based on dioptric power value, characteristic of posture of the wearer and characteristic of filtering means so that the vision comfort of the wearer is optimized when wearing the ophthalmic lens while observing a screen.

13 Claims, 1 Drawing Sheet

(56) References Cited

U.S. PATENT DOCUMENTS

| | | | |
|---|---|---|---|
| 2008/0094571 A1* | 4/2008 | Tarrant | G02C 7/06 |
| | | | 351/159.4 |
| 2008/0278676 A1* | 11/2008 | Croft | G02C 7/02 |
| | | | 351/44 |
| 2011/0001925 A1* | 1/2011 | Drobe | G02C 7/027 |
| | | | 351/204 |
| 2012/0307194 A1 | 12/2012 | Croft et al. | |

FOREIGN PATENT DOCUMENTS

| | | |
|---|---|---|
| FR | 2908899 | 5/2008 |
| FR | 2928744 | 9/2009 |
| JP | H 04-285907 | 10/1992 |
| JP | H 04-291315 | 10/1992 |
| JP | 2006-267316 | 10/2006 |
| JP | 2007-531610 | 11/2007 |
| JP | 2011-513798 | 4/2011 |
| JP | 2012-198256 | 10/2012 |
| JP | 2013-226397 | 11/2013 |
| JP | 2015-049338 | 3/2015 |

OTHER PUBLICATIONS

International Search Report and Written Opinion issued in International Application No. PCT/EP2016/057841, dated Jul. 7, 2016.

Jaschinski "The proximity-Fixation-Disparity curve and the preferred viewing distance at a visual display as an indicator of near vision fatigue," *Optometry and Vision Science*, 79(3): 158-169, (2002).

Search Report and Written Opinion issued in European Application No. 15305542, dated Sep. 24, 2015.

Office Action Issued in Corresponding Japanese Patent Application No. 2017-553169, dated Mar. 10, 2020.

* cited by examiner

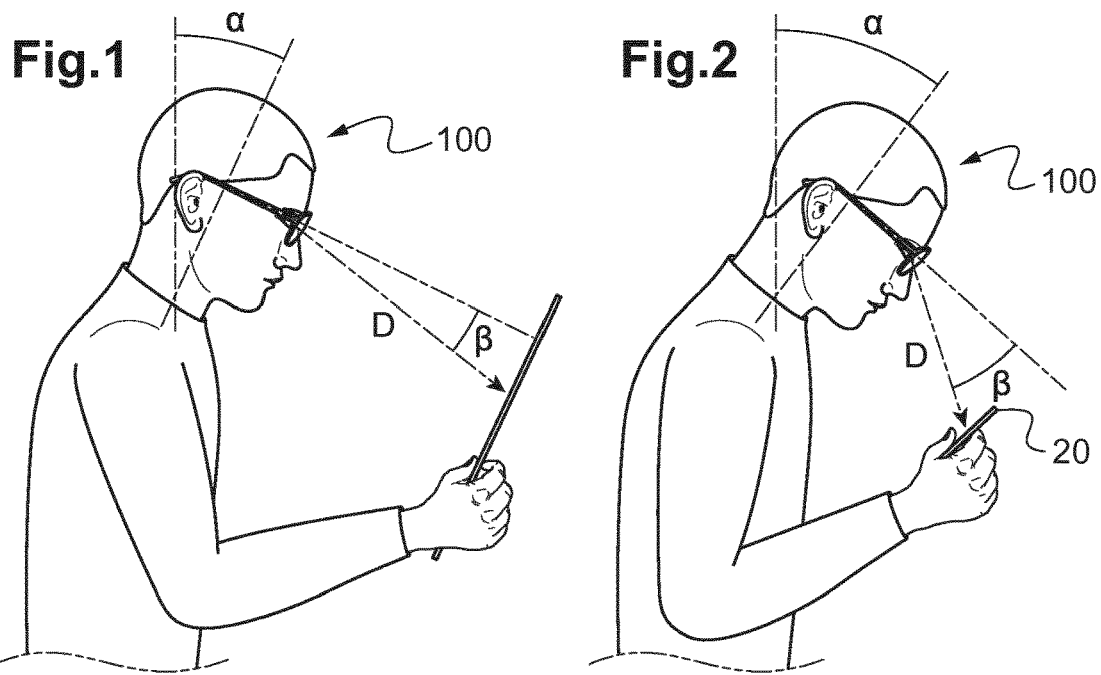
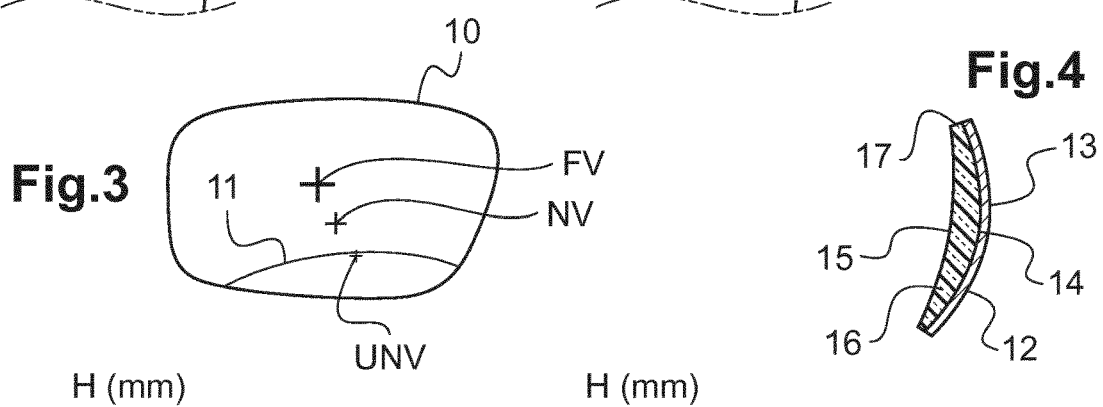
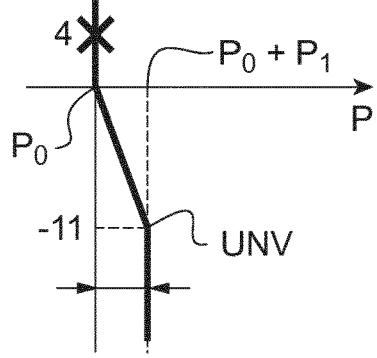
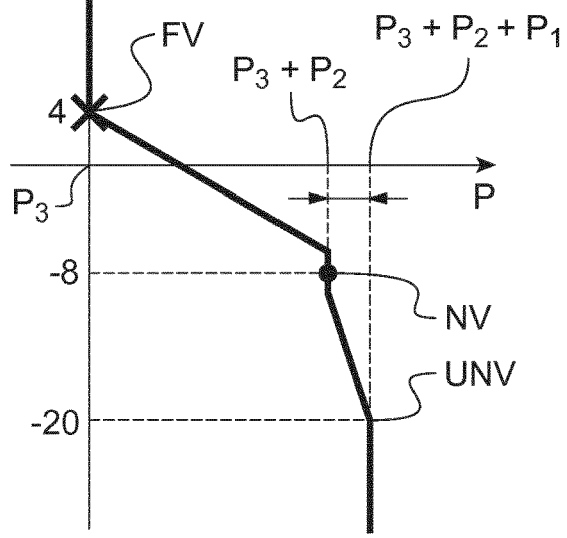

ic lens with a vision zone provided with filtering means that is dedicated to the reading on screens of digital devices.

OPHTHALMIC LENS AND METHOD FOR DETERMINING SUCH AN OPHTHALMIC LENS

CROSS-REFERENCE TO RELATED APPLICATIONS

This application is a national phase application under 35 U.S.C. § 371 of International Application No. PCT/EP2016/057841 filed 8 Apr. 2016, which claims priority to European Patent Application No. 15305542.1 filed 10 Apr. 2015. The entire contents of each the above-referenced disclosures is specifically incorporated by reference herein without disclaimer.

TECHNICAL FIELD TO WHICH THE INVENTION RELATES

The present invention relates in general to the preparation of eyeglasses suitable for improving vision comfort.

The invention applies more particularly to a method of determination of an ophthalmic lens suitable for improving vision comfort of a wearer who observes a screen of a digital device.

TECHNOLOGICAL BACKGROUND

A wearer of eyeglasses may be prescribed an optical power correction.

For presbyopic wearers, the value of the power correction is different for far-vision and near-vision, due to the difficulties of accommodation in near-vision. Thus, ophthalmic lenses suitable for presbyopic wearers are multifocal lenses, the most suitable being progressive multifocal lenses.

For the other wearers, the value of the power correction is generally the same on the entire surface of the lens.

Nowadays, digital devices such as smartphones, tablets, computers, TV become more and more indispensable.

The use of such digital devices has changed our behavior when reading something displayed on a screen of such a device.

Literature data on the use of screens show a great variability at the viewing distance (Jaschinski 2002 "The proximity-Fixation-Disparity curve and the preferred viewing distance at a visual display as an indicator of near vision fatigue". Optometry and Vision Science; Vol. 79, No. 3, pp 158-169). In this paper, authors measured the distance to the screen for 40 individuals free to place their screen as comfortable as possible. Results showed that the distance measured between the eyes of the wearer and the screen depends on the size of the screen.

Therefore, there is a need for an ophthalmic lens that is adapted to the individual variability in screen uses, mainly for new digital screens.

One object of the present invention is to provide such ophthalmic lenses for improving the vision comfort of a wearer when reading a text or working with new digital screens.

OBJECT OF THE INVENTION

The object of the present invention consists in a method of determining an ophthalmic lens suitable for improving vision comfort of a wearer when observing a screen, the ophthalmic lens comprising a vision zone, the vision zone being provided with filtering means, wherein the method comprises the steps of:

determining at least one characteristic of posture of the wearer observing said screen, determining a dioptric power value associated to said vision zone allowing the wearer when wearing the ophthalmic lens to have an easier reading of said screen, determining at least one characteristic of filtering means to adjust the light exposure of the wearer to said screen, and determining the vision zone position based on said dioptric power value and said at least one characteristic of posture of the wearer so that the vision comfort of the wearer is optimized when wearing the ophthalmic lens while observing a screen.

The optical needs for reading on a paper document and for reading on a screen of a digital device are not the same.

Actually, the reading tasks are performed with an average lowering angle of gaze direction and average distance of:

18°—over 40 cm for paper documents;
20°—39 cm for tablet screens.
25°—33 cm for smartphone screens;

In addition, luminance and spectrum of light emitted by digital devices are different of usual natural or artificial lightening.

Indeed, the eyes have to focus more intensively in order to read pixelated characters displayed on a little screen, in order to look at very short distances and in order to focus quickly from a distance to another. Moreover, eyes have to endure more screen glare and are exposed to more harmful blue-violet light when the screen is held at a little distance of the eyes. Such conditions are likely to increase discomfort and/or eye strain ("visual fatigue") and to deteriorate the retinas.

That is why the purport of the invention is to determine an ophthalmic lens comprising a vision zone provided with filtering means (an "ultra near vision zone") that is dedicated to the reading on screens of digital devices. In multifocal lenses, this ultra near vision zone may be located under the near vision zone, directly under this near vision zone, with a lateral shift toward the nasal edge of the lens.

By providing the vision zone ("ultra near vision zone") with a specific dioptric power (the "extra power") and specific filtering means (the "filter"), the vision comfort of a wearer is improved when wearing the ophthalmic lens while observing a screen.

More particularly, the vision comfort is increased because:

the extra power associated to the vision zone reduces visual fatigue when reading on screens of digital devices, the extra power has a magnifying effect that facilitates the readability of small characters, the filtering means avoids the wearer to receive too much light from the screen, avoiding blur and glare and protecting retina from harmful light, and the posture of the wearer when wearing the ophthalmic while observing a screen is more comfortable.

Surprisingly, inventors observed that wearer with ophthalmic lenses determined according to the invention were less suffering of headache, tired eye, neck and shoulder pain when using digital devices.

In the following, the term "reading", either a text or on a screen, encompasses several activities like reading, looking at images, writing/texting which involve that the eye is focused on a digital screen.

Another advantage of the invention is to allow a presbyopic wearer to maintain his habit with paper documents that is to move the document away from his eyes in order to try to read little characters. Indeed, thanks to the magnifying effect of the extra power, the wearer may read little characters even if he moves the screen away from his eyes.

In this context, it may be noted that the location of the zone of the ophthalmic lens suitable for the reading on screens, may be different as a function of the different screens mostly used by the wearer (television monitor, desktop computer monitor, laptop screen, phablet screen, tablet screen, smartphone screen, watch screen).

According to further embodiments which can be considered alone or in combination:

the method comprises an additional step of determining the degree of presbyopia of the wearer, for instance selected from non presbyopic, pre-presbyopic, increasing presbyopia, and presbyopia, and said step of selecting an extra power is operated as a function of said degree of presbyopia. This degree of presbyopia can be measured by the objective amplitude of accommodation, as described in "Minus lens stimulated accommodative amplitude decreases sigmoidally with age: a study of objectively measured accommodative amplitude from age 3". Investigative Ophthalmology & Visual Science. Vol. 49, No. 7, pp 2919-2926;

the method comprises an additional step of determining the degree of eyestrain felt by the wearer, and said step of determining an extra power is operated as a function of said degree of eyestrain;

the method comprises an additional step of determining the age of the wearer, and said step of determining an extra power is operated as a function of said age;

the method comprises an additional step of determining the frequency of use of screens, and said step of determining an extra power is operated as a function of said frequency of use;

the screen is selected from various types: television monitor, desktop computer monitor, laptop screen, phablet screen, tablet screen, smartphone screen and/or watch screen, and the extra power is located on said ophthalmic lens in a position determined as a function of the type selected;

said characteristic of posture is selected from a wearer's eye-screen distance, a trunk angle, a head angle, a head in trunk angle, and a lowering gaze angle;

the extra power is located in the lower part of the ophthalmic lens, preferably in a zone corresponding to a lowering gaze angle greater than 21°;

the extra power is located in a zone determined as a function of characteristics of posture;

said extra power has a value comprised between 0.125 and 1 diopter;

said filter decreases the transmission of visible light through the ophthalmic lens by at least 5%, in a wavelength range that has a width greater than 10 nm;

each step of determining a characteristic of posture, determining an extra power, and determining a filter is implemented, at least in part, by a computer.

The invention also relates to an ophthalmic lens suitable for improving vision comfort of a wearer when observing a screen wherein the ophthalmic lens comprises a vision zone provided with filtering means based on:

a dioptric power value allowing the wearer when wearing the ophthalmic lens to have an easier reading of said screen, a characteristic of filtering means to adjust the light exposure of the wearer to said screen, so that, the vision zone being an ultra near vision zone, the vision comfort of the wearer is optimized when wearing the ophthalmic lens while observing a screen.

According to further embodiments which can be considered alone or in combination:

the ultra near vision zone provided with filtering means is based on at least a characteristic of posture of the wearer observing said screen, the ultra near vision zone corresponding to a lowering gaze angle β of the wearer observing said screen greater than 21°, the ultra near vision zone provided with filtering means is a stabilized vision zone;

the ophthalmic lens comprises at least at least one stabilized vision zone different from the ultra near vision zone and selected from far vision zone, intermediate vision zone and near vision zone;

the ultra near vision zone has a dioptric power value larger than 0.125, the ophthalmic lens comprises a front main face and a rear main face, and in that said filter is laid on at least a part of said front main face and/or said rear main face;

said filter inhibits transmission of visible light by at least 5%, over at least a selected range of wavelengths that has a width greater than 10 nm and that is centered on a mean wavelength comprised between 420 nm and 450 nm or between 460 nm and 490 nm or between 485 nm and 515 nm or between 560 nm and 620 nm;

said filter has a mean reflection factor of at least 5%, over a range of wavelengths comprised between 420 nm and 450 nm or between 460 nm and 490 nm or between 485 nm and 515 nm or between 560 nm and 600 nm or between 580 nm and 620 nm;

the ophthalmic lens shows a mean light reflection factor on said part of said front main face and/or said rear main face that is lower than 1%;

said filter is selected from absorption filters, reflection filters, and interferential filters.

The invention also relates to a method of providing a wearer of an ophthalmic lens with a rating of said ophthalmic lens, comprising the steps of:

identifying an extra power allowing the wearer to have an easier reading of a screen, identifying a filter that adjusts the exposure of the wearer to said screen, determining the rating as a function of said extra power and said filter, and providing said rating for the wearer.

DETAILED DESCRIPTION OF AN EMBODIMENT

The following description with reference to the accompanying drawings, given by way of non-limiting example makes it clear what the invention consists in and how it can be reduced to practice.

In the accompanying drawings:

FIG. 1 is a schematic view of a wearer who reads a paper document;

FIG. 2 is a schematic view of a wearer who reads a document on a screen of a digital device;

FIG. 3 is a schematic face view of an ophthalmic lens according to the invention;

FIG. 4 is a schematic side view of the ophthalmic lens of FIG. 3;

FIG. 5 is a graphic illustrating the variation of the optical spherical power of an "unifocal" lens along a vertical axis of this lens;

FIG. 6 is a graphic illustrating the variation of the optical spherical power of a multifocal lens along a vertical axis of this lens.

In the remainder of the description, terms like «up», «bottom», «horizontal», «vertical», «above», «below», or other words indicating relative position may be used. These terms are to be understood in the wearing conditions of the lens.

Notably, the "lower" part of the lens corresponds to the zone of the lens through which the wearer looks at when his gaze direction is directed towards the top of its nose (with a gaze direction angle β>0°).

The following definitions are provided to describe the present invention.

The Frankfort plane is defined as being the plane containing the bottom orbit point and the porion of the wearer, where the porion is the highest point in the skull of the acoustic meatus, which corresponds to the tragion of the ear.

When a wearer is looking at a paper document (FIG. 1) or a screen of a digital device (see FIG. 2), the posture of the wearer may be defined by various characteristics among:
- a wearer's eye-screen distance D,
- a trunk angle,
- a head angle α,
- a head in trunk angle, and
- a lowering gaze angle β.

The wearer's eye-screen distance D is the distance between the eyes of the wearer and the center of the screen 20.

The trunk angle (not shown in the figures) is the angle between a vertical axis and the mean axis of the trunk of the wearer.

The head angle α is the angle between a horizontal plane and the Frankfort plane.

The head in trunk angle is the sum of the trunk angle plus the head angle.

The lowering gaze angle β is the angle between the Frankfort plane and the plane that comprises the optical axes of the eyes of the wearer.

Here, we consider that the roll angle of the head of the wearer 100 is null.

Prescription data are known in the art.

Prescription data refers to one or more data obtained for the wearer and indicating for each eye a prescribed far vision mean refractive power, and/or a prescribed astigmatism value and/or a prescribed astigmatism axis and/or a prescribed addition suitable for correcting the ametropia and/or presbyopia of each eye. Prescription data also refers to one or more data obtained for the wearer and indicating for each eye a prescribed near vision mean refractive power, and/or a prescribed astigmatism value and/or a prescribed astigmatism axis and/or a prescribed degression suitable for correcting the ametropia and/or presbyopia of each eye.

According to the invention, the ophthalmic lens may be selected from uncorrective (also called plano) or corrective lenses. Corrective lenses may be progressive and degressive lenses; monofocal, bifocal, or more generally multifocal lenses. The lens may be designed to fit a spectacles frame so as to protect the eye and/or correct the sight.

Such an ophthalmic lens 10 comprises a core 16 (see FIG. 4) that has a front main face 14, a rear main face 15 and an edge 17.

The core 16 of the lens is shaped to impart optical properties to the ophthalmic lens 10, which correspond to the prescription data of the wearer.

The optical correction power of the ophthalmic lens 10 is defined by its spherical, cylindrical, and prismatic refractive power properties. It will be understood that such an optical definition gives a scope that is more general than a definition that is purely in terms of area: it defines the overall effect of the refractive power of the lens on an incident light ray, that results from the algebraic sum of the refractive powers acting in succession on the front and rear faces of the lens.

An unifocal lens usually has a spherical refractive power, a cylindrical refractive power and a prismatic refractive power that are constant on the entire surface of the lens. Such an unifocal lens is marked on one of its main faces by a cross, that shows the position of a characteristic point of the lens (for instance the optical center), and by an horizontal line.

A multifocal lens usually has a spherical refractive power, a cylindrical refractive power and a prismatic refractive power that are constant on the upper part of the lens (the far vision zone), and a spherical refractive power that varies in the bottom part of the lens (particularly in a near vision zone). Such a multifocal lens is defined in particular by three main optical magnitudes:
- a "spherical power addition" equal to the variation in spherical power between a reference point FV of the far vision zone and a reference point NV of the near vision zone (see FIG. 3);
- a "nominal power" equal to the power at said reference point FV of the far vision zone; and
- a nominal astigmatism equal to the cylindrical refractive power at said reference point FV of the far vision zone.

This multifocal lens is usually marked on one of its faces by various signs that shows the positions of the reference points FV, NV.

In the context of the instant invention, we also consider that the (unifocal or multifocal) ophthalmic lens 10 comprises an "extra power P1" in an "ultra near vision zone" 11 located in the lower part of the ophthalmic lens, in a zone corresponding to a lowering gaze angle used to read on a digital screen.

The far vision zone of the lens, located around the reference point FV, is the zone through which the wearer is looking at an object situated at a distance greater than 1 meter (for instance a TV screen . . . ).

The near vision zone of the lens, located around the reference point NV, is the zone through which the wearer is looking at an object situated at a distance comprised between 40 centimeters and 1 meter (for instance a paper document, a screen of a laptop . . . ).

According to the invention, the ultra near vision zone 11 provided on the lens, below a reference point UNV, is the zone through which the wearer is looking at an object situated at a distance smaller than 40 centimeters: for instance a screen of phablet, tablet, smartphone or watch. This zone corresponds to a lowering gaze angle β greater than 21°.

In a specific embodiment, the ultra near vision zone 11 provided on the lens is the zone through which the wearer is looking at an object situated at a distance smaller than 35 centimeters: for instance a smartphone.

In this ultra near vision zone, the extra power $P_1$ is defined as a dioptric power value equal to the variation in spherical power between:
- the optical center and the reference point UNV of the ultra near vision zone in the case of an unifocal lens, or the reference point NV of the near vision zone and the reference point UNV of the ultra near vision zone in the case of a multifocal lens.

In the case of a unifocal lens, as shown in FIG. 5, the extra power $P_1$ is the value of spherical power added to the value of the main spherical power $P_0$ of the lens in the remainder of the surface of the lens. In a specific embodiment, spherical power $P_0$ is zero when the wearer doesn't need an optical correction. Thus, it is understood that the term unifocal is not really proper, but it is used to make this description clearer.

On this figure, we may observe that the main spherical power $P_0$ is constant from the top of the lens to 4 mm under the marked cross of the lens. Then, the spherical power continuously increases to a point situated 15 mm below the marked cross of the lens. At this point (that is the reference point UNV), the spherical power of the lens is equal to the sum of the main spherical power $P_0$ plus the extra power $P_1$. Then, the spherical power remains constant to the bottom of the lens, defining the "ultra near vision" zone.

Specifically, when the "ultra near vision" zone has a constant power, it is a stabilized vision zone. In some embodiments, ophthalmic lens according to the invention comprises a stabilized vision zone provided with filtering means.

In the case of a multifocal lens, as shown in FIG. 6, the extra power $P_1$ is equal to the value of spherical power added to the value of the spherical power of the lens at the reference point NV.

On this figure, we may observe that the spherical power of the lens is constant from the top of the lens to the reference point FV of the lens (marked cross), defining a first stabilized vision zone. Then, the spherical power continuously increases to a point situated 12 mm below the reference point FV. At this point (that is really near from the reference point NV), the spherical power of the lens is equal to the sum of the nominal power $P_3$ plus the spherical power addition $P_2$. The spherical power remains constant on 2 mm height defining a second stabilized vision zone, and then it increases continuously to a point situated 12 mm below the reference point NV. At this point (that is the reference point UNV), the spherical power of the lens is equal to the sum of the nominal power $P_3$ plus the spherical power addition $P_2$ plus the extra power $P_1$. Then, the spherical power remains constant to the bottom of the lens, defining a third stabilized vision zone.

Specifically, the ophthalmic lens obtained by the invention comprises at least one stabilized vision zone selected from far vision zone, intermediate vision zone and near vision zone.

In these two cases illustrated on FIGS. 5 and 6, the extra power $P_1$ has a value comprised between 0.125 and 1 diopter.

Actually, the invention relates to a method of determining an ophthalmic lens 10 suitable for improving vision comfort of a wearer 100 when observing a screen 20, the ophthalmic lens comprising a vision zone, the vision zone being provided with filtering means 12, wherein the method comprises the steps of:
- determining at least one characteristic of posture $\alpha$, $\beta$, D of the wearer 100 observing said screen 20,
- determining a dioptric power value $P_1$ associated to said vision zone allowing the wearer 100 when wearing the ophthalmic lens to have an easier reading of said screen 20,
- determining at least one characteristic of filtering means 12 to adjust the light exposure of the wearer 100 to said screen 20, and
- determining the vision zone based on said dioptric power value, said at least one characteristic of posture of the wearer and said at least one characteristic of filtering means so that the vision comfort of the wearer is optimized when wearing the ophthalmic lens while observing a screen.

This method is operated as follows.

In a first step, an optician acquires at least one of the following characteristics:
- the degree of presbyopia of the wearer, for instance selected from the following list: non presbyopic, pre-presbyopic, increasing presbyopia, and presbyopia,
- the degree of eyestrain felt by the wearer, for instance selected from the following list: low, mid, high,
- the age of the wearer, and
- the frequency of use of digital devices, for instance selected from the following list: television monitor, desktop computer monitor, laptop screen, phablet screen, tablet screen, smartphone screen and/or watch screen.

Here, he acquires all these characteristics by asking questions to the wearer, and then he enters these characteristics in a computer. In another embodiment, the wearer may enter these characteristics in the computer by himself.

In a second step, the optician acquires the prescriptions of the wearer.

We may consider the case of a presbyopic wearer.

In this case, the optician acquires a "spherical power addition", a "nominal power" and a nominal astigmatism.

He also acquires (for instance by measuring and calculating the necessary data) the positions of the reference points FV and NV.

Because these operations are well known to those skilled in the art, they will not be developed in the present description.

In a third step, the optician acquires a side image of the wearer looking at the screen 20 of his digital device (here a smartphone), thanks to a camera or to any device suitable for taking such a picture. The acquired image is represented in FIG. 2.

He may then measure on this image various posture characteristics and enter these characteristics in the computer.

But, in a preferred embodiment, the image is processed by the computer, that automatically measures the wearer's eye-screen distance D, the head angle $\alpha$, and the lowering gaze angle $\beta$.

Then, the computer automatically calculates the value of the extra power $P_1$, the position of the reference point UNV (also called position of the extra power), and the kind of filter 12 needed by the wearer.

We may first consider the determination of the location of the reference point UNV.

For instance, if the digital device is a smartphone, the reference point UNV may be located at the points shown in FIG. 5 and 6.

The position of the reference point UNV may be corrected as a function of the wearer's eye-screen distance D and the lowering gaze angle $\beta$.

For instance, if the wearer's eye-screen distance D is lower than 33 cm and the lowering gaze angle $\beta$ is greater than 25°, the position of the reference point UNV may be located 1 mm below the position shown in FIG. 5 or 6.

The position of the reference point UNV may be corrected as a function of the kind of digital device used by the wearer and of the frequency of use of digital devices.

For instance, if the wearer is frequently writing on a smartphone the reference point UNV may be located 1 mm above the positions shown in FIG. 5 or 6.

We may now consider the determination of the value of the extra power $P_1$ for a non presbyopic wearer.

In this case, in which the lens is unifocal, the extra power $P_1$ may be equal to:

0.4 diopter if the age of the wearer is comprised between 20 and 34 years old, 0.6 diopter if the age of the wearer is comprised between 35 and 44 years old, or 0.85 diopter if the age of the wearer is comprised between 45 and 50 years old.

The value of the extra power $P_1$ may be corrected as a function of the wearer's eye-screen distance D and the lowering gaze angle β.

For instance, if the wearer's eye-screen distance D is lower than 33 cm and the lowering gaze angle β is greater than 25°, the value of the extra power $P_1$ may be increased by 0.1 diopter.

The value of the extra power $P_1$ may also be corrected as a function of the degree of eyestrain felt by the wearer and of the frequency of use of digital devices.

For instance, the value of the extra power $P_1$ may be increased by 0.05 diopter if the wearer fells a mid eyestrain or by 0.1 diopter if the wearer fells a high eyestrain.

This value may also be increased by 0.1 diopter if the frequency of use of digital devices is high.

We also may consider the determination of the value of the extra power $P_1$ for a presbyopic wearer.

In this case, in which the lens is multifocal, the extra power $P_1$ may be comprised between 0.125 and 0.5 diopter and may be calculated as a function of the field of view needed by the wearer.

For instance, this extra power $P_1$ may be equal to:

0.5 diopter if the wearer needs strong magnification and narrow field of view (intensive use of digital screens), 0.25 diopter if the wearer need good magnification while having a good field of view (simultaneous use of digital screens at different distances), or 0.125 diopter if the wearer need magnification while keeping a wide field of view (use of digital screens at short distance while looking at TV).

For all wearers, presbyopic or non presbyopic, the position of the reference point UNV may be corrected as a function of the extra power P1. Indeed, if the extra power P1 is great (for instance larger than or equal to 0.5 diopter), the reference point UNV may be shifted below the position initially determined (for example of 1 mm). Else, the reference point UNV is not shifted.

The value of the extra power $P_1$ and the position of the reference point UNV may be corrected as a function of the degree of eyestrain felt by the wearer and of the frequency of use of digital devices, as stated hereabove.

This ophthalmic lens 10 comprises also a filter 12, 13 laid on at least a part of said front main face 14 and/or said rear main face 15.

Advantageously, this filter 12, 13 covers the entire surface of one face (here the font main face 14) of the lens 10.

Filters are either based on absorption or on reflection.

Absorption filters are configured to inhibit transmission by partial or total absorption of light. They include colour filters obtained with dyes and/or pigments, photochromic filters, polarizing filters. These filters may be also controlled by an external signal like electrochromic filters. The choice of material for absorption filter defines a specific absorption spectrum of light. When dyes or pigments are used, they may be incorporated in the ophthalmic lens substrate or in a coating deposited on the ophthalmic lens substrate, such as a primer, an adhesive layer, an imbibition layer or a hard coat.

Reflection filters are configured to inhibit transmission by partial or total reflection of light. They include multilayered filters, in which layers of low refractive index material alternate with layers of high refractive index material. These layers may be organic or inorganic. Depending on number of layers (from 4 to several hundreds), refractive index (from 1.3 to 2.5 for mineral material, from 1.4 to 1.8 for organic material) of each layer and thickness of each layer, a reflection filter has a specific reflection spectrum. Multilayered filters are often named interferential filters.

Anti-reflective filters (or "coatings") are widely used for minimizing the reflection from lenses in order to improve wearer's comfort as well as aesthetics. Generally, the key objective of antireflection design is to reach a "reflectance" as low as possible, while taking into account different constraints, e.g., manufacturing process, color robustness and number of layers, etc. When deposited on a transparent substrate, the function of such a coating is to reduce its light reflection and therefore to increase its light transmission. A substrate thus coated will therefore have its transmitted light/reflected light ratio increased, thereby improving the visibility of objects placed behind it. When it is sought to achieve a maximum antireflection effect, it is then preferable to provide both faces (front and rear faces) of the substrate with this type of coating.

This anti-reflective coating is usually used in the ophthalmic field. Accordingly, traditional anti-reflective coatings are designed and optimized to reduce reflection on the lens surface in the visible region, typically within the spectrum range of from 380 to 780 nm.

As reflectance is a function of wavelength, and because the human eye has different sensitivity for various wavelength, the mean light reflection Rv of anti-reflective design is described by following equation:

$$R_V = \frac{\int_{380}^{780} R(\lambda) \cdot V(\lambda) \cdot D_{65}(\lambda) \cdot d\lambda}{\int_{380}^{780} V(\lambda) \cdot D_{65}(\lambda) \cdot d\lambda}$$

where R(λ) is the reflectance at wavelength of λ, V(λ) is the eye sensitivity function V(λ) defined in standard CIE 1931, D65(λ) is the daylight illuminant defined in standard CIE S005/E-1998.

All filters, by absorption or by reflection, may be designed with an absorption or reflection spectrum providing a specific filtering effect, colour balancing, contrast enhancement or anti glare.

Last, we may consider the selection of the kind of filter 12 used on the core of the ophthalmic lens 10.

Here, the filter 12 is configured to selectively inhibit transmission, through the lens of at least one selected range of wavelengths of incident light in the visible light spectrum at an inhibition rate of at least 5%. In particular, the selective optical filtering means is further configured to transmit at least 8% of incident light of the visible spectrum outside the at least one selected range of wavelengths. In some embodiments, inhibition rate of filter 12 is at least 10%, or at least 20% or at least 35% or at least 50% or at least 65% or at least 80%.

In some embodiments, the selected range of wavelength is narrow with a width greater than 10 nm and smaller than 150 nm, preferably smaller than 100 nm, more preferably smaller than 70 nm.

In another embodiment, filter 12 inhibits transmission of visible light by at least 5%, over at least one of the following ranges of wavelengths:
- a first range of wavelengths that has a width of at least 20 nm and that is centered on a mean wavelength equal to 435 nm, in order to inhibit blue-violet light,
- a second range of wavelengths that have a width of at least 20 nm and that is centered on mean wavelengths equal to 475 nm, in order to increase the red/green contrast,
- a third range of wavelengths that have a width of at least 20 nm and that is centered on mean wavelengths equal to 580 nm, in order to increase the red/green contrast,
- a fourth range of wavelengths that has a width of at least 20 nm and that is centered on a mean wavelength equal to 500 nm, in order to increase the blue/green contrast, and
- a fifth range of wavelengths that has a width of at least 20 nm and that is centered on a mean wavelength equal to 600 nm, in order to reduce the glare.

The ranges of wavelengths inhibited by the filter 12 are selected as a function of the kind of digital device commonly used by the wearer.

For instance, the first range of wavelengths will automatically be selected for wearers who often use smartphones, and the fifth range of wavelengths will be selected for wearers who use digital devices that have no means for automatically reduce the lighting intensity of the screen in the darkness.

In some embodiments, filter 12 is a reflection filter. In particular, filter 12 has a mean reflection factor of at least 5%, over a range of wavelengths comprised between 420 nm and 450 nm or between 460 nm and 490 nm or between 485 nm and 515 nm or between 560 nm and 600 nm or between 580 nm and 620 nm.

In a particular embodiment, filter 12 shows a mean light reflection factor Rv that is lower than 1% for an angle of incidence lower than 30°.

In an additional embodiment, it is provided to the ophthalmic lens 10 a rating Ra for indicating to the wearer the performance of the lens especially for reading on screens of digital devices.

The rating Ra is based on a ratio which quantifies:
- the protection provided by the ophthalmic lens 10 to the wearer relative to blue-violet light emitted by such screens, and
- the performance of magnification of the ophthalmic lens thanks to the extra power.

The method comprises the steps of identifying the extra power P1 and the kind of filter 12 of the lens, determining the rating Ra as a function of said extra power P1 and said filter 12, then providing to the wearer 100 the rating Ra of the lens.

Another aspect of the invention is the use of an ophthalmic lens comprising a vision zone, the vision zone comprising filtering means based on:
- at least a characteristic of posture $\alpha$, $\beta$, D of the wearer 100 observing said screen 20,
- a dioptric power value $P_1$ allowing the wearer 100 when wearing the ophthalmic lens to have an easier reading of said screen,
- a characteristic of filtering means 12 to adjust the light exposure of the wearer 100 to said screen 20, so that the vision comfort and/or the eyestrain and/or the postural comfort of the wearer when wearing the ophthalmic lens while observing a screen is improved.

Particularly, the use of the ophthalmic lens according to the invention is suitable for emerging uses of digital devices, especially when several digital devices of different sizes are used simultaneously, for instance texting while watching TV, texting while working on a computer, working or playing video games with multiple digital screens.

The use of the ophthalmic lens according to the invention is also suitable for use of digital devices at very near distance, such as reading or working on a smartphone or a tablet, taking pictures with a digital camera or a smartphone or a tablet.

The use of the ophthalmic lens according to the invention is particularly suitable for intensive and/or long use of digital devices.

The invention claimed is:

1. A method of determining an ophthalmic lens suitable for improving vision of a wearer when observing a screen, the ophthalmic lens comprising a far vision zone, a near vision zone, and a stabilized ultra near vision zone, the stabilized ultra near vision zone being provided with filtering means, being distinct from the far vision zone and from the near vision zone, and corresponding to a lowering gaze angle of the wearer observing the screen greater than 21°, and to a zone through which the wearer looks at said screen at a distance small than 40 centimeters, wherein the method comprises the steps of:
- determining at least one characteristic of posture of the wearer observing said screen, wherein the at least one characteristic of posture is a trunk angle, a head angle, a head in trunk angle, or a lowering gaze angle,
- determining the degree of presbyopia of the wearer,
- determining a dioptric power value associated to said vision zone as a function of said degree of presbyopia, said dioptric power value being distinct from the one of said near vision zone,
- determining at least one characteristic of said filtering means to adjust the light exposure of the wearer to said screen, and
- determining the vision zone based on said dioptric power value, said at least one characteristic of posture and said at least one characteristic of filtering means.

2. The method of determining according to claim 1, wherein:
- the method comprises an additional step of determining the degree of eyestrain felt by the wearer, and
- said step of determining a dioptric power value or determining a filter is operated as a function of said degree of eyestrain.

3. The method of determining according to claim 1, wherein:
- the method comprises an additional step of determining the age of the wearer, and
- said step of determining a dioptric power value or determining a filter is operated as a function of said age.

4. The method of determining according to claim 1, wherein:
- the method comprises an additional step of determining the frequency of use of said screen, and
- said step of determining a dioptric power value or determining a filter is operated as a function of said frequency of use.

5. The method of determining according to claim 1, wherein:

the screen is selected from various types: television monitor, desktop computer monitor, laptop screen, phablet screen, tablet screen, smartphone screen or watch screen, and the dioptric power value is located on said ophthalmic lens in a position determined as a function of the type selected.

6. The method of determining according to claim 1, wherein said filter decreases the transmission of visible light through the ophthalmic lens by at least 5%, in a wavelength range that has a width greater than 10 nm.

7. The method of determining according to claim 1, wherein each step of determining a characteristic of posture, determining a dioptric power value, and determining a filter is implemented, at least in part, by a computer.

8. An ophthalmic lens suitable for improving vision of a wearer when observing a screen wherein the ophthalmic lens comprises a far vision zone, a near vision zone, and a stabilized ultra near vision zone, the stabilized ultra near vision zone being provided with filtering means, being distinct from the far vision zone and from the near vision zone, and corresponding to a lower gaze angle of the wearer observing the screen greater than 21°, and to a zone through which the wearer looks at said screen at a distance smaller than 40 centimeters, said stabilized ultra near vision zone being designed based on:

at least one characteristic of posture of the wearer observing said screen, wherein the at least one characteristic of posture is a trunk angle, a head angle, a head in trunk angle, or a lowering gaze angle, a degree of presbyopia of the wearer, a dioptric power value function of said degree of presbyopia, said dioptric power value being distinct from the one of said near vision zone, and a characteristic of filtering means to adjust the light exposure of the wearer to said screen.

9. The ophthalmic lens according to claim 8 wherein the vision zone provided with filtering means is a stabilized vision zone.

10. The ophthalmic lens according to claim 8 wherein the ophthalmic lens comprises at least one stabilized vision zone selected from far vision zone, intermediate vision zone and near vision zone.

11. The ophthalmic lens according to claim 8, wherein the ophthalmic lens comprises a front main face and a rear main face, and in that said filter is laid on at least a part of said front main face or said rear main face.

12. The ophthalmic lens according to claim 11, wherein said filter has a mean reflection factor of at least 5%, over a range of wavelengths comprised between 420 nm and 450 nm.

13. A method of providing a wearer of an ophthalmic lens with a rating of said ophthalmic lens, wherein the ophthalmic lens comprises a far vision zone, a near vision zone, and a stabilized ultra near vision zone, the stabilized ultra near vision zone being provided with filtering means, being distinct from the far vision zone and from the near vision zone, and corresponding to a lowering gaze angle of the wearer observing the screen greater than 21°, and to a zone through which the wearer looks at said screen at a distance smaller than 40 centimeters, wherein the method comprises the steps of:

determining at least one characteristic of posture of the wearer observing said screen, wherein the at least one characteristic of posture is a trunk angle, a head angle, a head in trunk angle, or a lowering gaze angle, and, on the basis of this characteristic, determining the degree of presbyopia of the wearer, identifying a dioptric power value as a function of said degree of presbyopia, said dioptric power value being distinct from the one of said near vision zone, identifying a filter that adjusts the exposure of the wearer to said screen, determining the rating as a function of said dioptric power value and said filter, and providing said rating for the wearer.

* * * * *